United States Patent
Wu et al.

(10) Patent No.: US 9,056,827 B2
(45) Date of Patent: Jun. 16, 2015

(54) METHOD OF SYNTHESIZING POLYOL ACETATE BY USING CATALYST OF IONIC LIQUID HETEROPOLY ACID

(75) Inventors: Jung-Chung Wu, Chiayi (TW); Jen-Chun Chang, Chiayi (TW); Ming-Yu Huang, Chiayi (TW); Jann-Chen Lin, Chiayi (TW)

(73) Assignee: CPC CORPORATION, TAIWAN, Taipei (TW)

( * ) Notice: Subject to any disclaimer, the term of this patent is extended or adjusted under 35 U.S.C. 154(b) by 681 days.

(21) Appl. No.: 13/367,460

(22) Filed: Feb. 7, 2012

(65) Prior Publication Data

US 2013/0109882 A1    May 2, 2013

(51) Int. Cl.
*C07C 67/08* (2006.01)
*B01J 31/02* (2006.01)

(52) U.S. Cl.
CPC ............. *C07C 67/08* (2013.01); *B01J 31/0279* (2013.01); *B01J 31/0284* (2013.01); *B01J 2231/49* (2013.01)

(58) Field of Classification Search
CPC ....................................................... C07C 67/08
See application file for complete search history.

(56) References Cited

U.S. PATENT DOCUMENTS

2004/0035293 A1* 2/2004 Davis, Jr. .................. 95/140

* cited by examiner

*Primary Examiner* — Joseph Kosack
(74) *Attorney, Agent, or Firm* — Jackson IPG PLLC; Demian K. Jackson (57) ABSTRACT

The present invention uses a nitrogen-containing organic compound to be reacted with an alkyl sultone to obtain a zwitterion compound. The zwitterion compound is reacted with a heteropoly acid (HPA) to obtain an ionic liquid HPA (IL-HPA). The IL-HPA is used for acetylation of polyol and HOAc for obtaining polyol acetate. The IL used in the reaction can be recycled. Thus, problems of product separation, waste acid handling, and corrosion of facilities are solved and production through esterification is improved with a green catalysis.

13 Claims, 10 Drawing Sheets

| batch | PPS/TPA mole ratio | products, mole% | | | | |
|---|---|---|---|---|---|---|
| | | GL | GMA | GDA | GTA |
| GTA-1 | 3.0 | 0 | 5.4 | 51.4 | 43.2 |
| GTA-2 | 2.5 | 0 | 4.7 | 49.2 | 46.1 |
| GTA-3 | 2.0 | 0 | 3.7 | 46.3 | 50.0 |
| GTA-4 | 1.5 | separation not processed | | | | |

FIG.4

| batch | TPA sintering temperature (°C) | product distribution (mole%) | | | | | note |
|---|---|---|---|---|---|---|---|
| | | GL | GMA | GDA | GTA | | |
| GTA-3 | --- | 0 | 3.7 | 46.3 | 50.0 | | absorbed with 12.4wt% water |
| GTA-5 | 110 | 0 | 3.6 | 44.0 | 52.4 | | not absorbed with water |
| GTA-6 | 200 | 0 | 2.9 | 42.1 | 55.0 | | remove part of crystallized water |
| GTA-7 | 250 | 0 | 1.7 | 36.9 | 61.4 | | |
| GTA-8 | 300 | 0 | 1.2 | 36.6 | 62.2 | | |
| GTA-9 | 350 | 0 | 1.2 | 36.4 | 62.4 | | |
| GTA-10 | 400 | 0 | 1.0 | 36.3 | 62.7 | | remove crystallized water |

FIG.5

| batch | HOAc/GL mole ratio | products distribution (mole%) | | | | |
|---|---|---|---|---|---|---|
| | | GL | GMA | GDA | GTA |
| GTA-11 | 5 | 0 | 3.7 | 50.3 | 45.0 |
| GTA-8 | 10 | 0 | 1.2 | 36.6 | 62.2 |
| GTA-12 | 15 | 0 | 0.3 | 32.3 | 67.4 |
| GTA-13 | 20 | 0 | 0.2 | 22.8 | 77.0 |
| GTA-14 | 25 | 0 | 0 | 14.1 | 85.9 |

FIG.6

| batch | IL amount (mole%) | products distribution (mole%) | | | | note |
|---|---|---|---|---|---|---|
| | | GL | GMA | GDA | GTA | |
| GTA-15 | 1.5 | 0 | 3.5 | 46.0 | 50.5 | |
| GTA-16 | 2.5 | 0 | 2.3 | 40.0 | 57.7 | |
| GTA-8 | 5.0 | 0 | 1.2 | 36.6 | 62.2 | |
| GTA-17 | 7.5 | 0 | 0.5 | 33.7 | 65.8 | |
| GTA-18 | --- | 0 | 3.0 | 43.4 | 53.6 | 10 mole% PPS-$H_2SO_4$ |
| GTA-19 | --- | 0 | 2.8 | 43.2 | 55.0 | 10 mole% PPS-$CF_3SO_3H$ |

FIG.7

| batch | reaction temp./time | products distribution (mole%) | | | |
|---|---|---|---|---|---|
| | | GL | GMA | GDA | GTA |
| GTA-20 | 85°C / 2 hr | 0 | 1.5 | 38.0 | 60.5 |
| GTA-8 | 105°C / 2 hr | 0 | 1.2 | 36.6 | 62.2 |
| GTA-21 | 125°C / 2 hr | 0 | 0.8 | 35.7 | 63.5 |
| GTA-22 | 105°C /0.5hr | 0 | 3.7 | 46.0 | 50.3 |
| GTA-23 | 105°C / 1 hr | 0 | 1.6 | 40.2 | 58.2 |
| GTA-8 | 105°C / 2 hr | 0 | 1.2 | 36.6 | 62.2 |
| GTA-24 | 105°C / 4 hr | 0 | 1.2 | 36.3 | 62.7 |
| GTA-25 | 105°C / 6 hr | 0 | 1.1 | 36.1 | 62.8 |

FIG.8

| batch | HOAc/GL mole ratio | products distribution (mole%) | | | | | note |
|---|---|---|---|---|---|---|---|
| | | GL | GMA | GDA | GTA | | |
| GTA-26 | 10 | 0 | 1.1 | 36.5 | 62.4 | | first reaction |
| GTA-27 | 10 | 0 | 1.3 | 36.3 | 62.4 | | second reaction |
| GTA-28 | 10 | 0 | 1.3 | 36.5 | 62.2 | | third reaction |
| GTA-29 | 10 | 0 | 0 | 13.2 | 86.8 | | remove water and HOAc after reaction and then re-add HOAc |

FIG.9

| Batch | HOAc/polyol mole ratio | products distribution (mole%) | | | | | | note |
|---|---|---|---|---|---|---|---|---|
| | | EGMA | EGDA | PGMA | PGDA | DEGMA | DEGDA | |
| GTA-30 | 15 | 3.8 | 96.2 | --- | --- | --- | --- | EG |
| GTA-31 | 15 | --- | --- | 14.0 | 86.0 | --- | --- | PG |
| GTA-32 | 15 | --- | --- | --- | --- | 17.6 | 82.4 | DEG |

METHOD OF SYNTHESIZING POLYOL ACETATE BY USING CATALYST OF IONIC LIQUID HETEROPOLY ACID

TECHNICAL FIELD OF THE INVENTION

The present invention relates to polyol acetylation; more particularly, relates to using a Bronsted acid ionic liquid (IL) as a catalyst to process polyol acetylation, where problems of product separation, waste acid handling, and corrosion of facilities are solved and production through esterification is improved with a green catalysis.

DESCRIPTION OF THE RELATED ARTS

With acidic catalyst, polyol and acetic acid (HOAc) can be synthesized to obtain polyol acetate, like ethylene glycol acetate (EGA), diethylene glycol acetate (DEGA), propylene glycol acetate (PGA), glycerol acetate (GLA), etc. For example, polyol monoalkyl ether can be used as a feed for synthesizing polyol monoalkyl ether acetate. This kind of glycol acetate or ether acetate compound is a solvent having a high boiling temperature and multiple functions, which has a high dissolving power to be widely used in products like vehicle sprayer, surface coating, printing, aqua coating, paint remover, rinsing agent, etc. Besides, glycerol triacetate (GTA) is not only used to improve cold filter plugging point and viscosity of biodiesel; but also is used in fields of cosmetics, food industry and polyol plasticizer. In the future, polyol-series ether compounds will play important roles in markets of oxygen-containing solvents and plasticizer.

For esterification of acid and alcohol, liquid acidic catalyst is used in most cases, like sulfuric acid ($H_2SO_4$), hydrofluoric acid (HF), p-toluenesulfonic acid (p-$CH_3$—$C_6H_4$—$SO_3H$, P-TSA), etc. Although esterification can be effectively processed, the whole fabrication procedure still has problem in waste acid handling. If a solid acid is used, the problem can be reduced. A common solid acid catalyst of polymer acid, like Amberlyst 15 and Nafion NR-50, can effectively help the esterification process. Yet, because its heat tolerance is lower than 150° C., its application is limited. If inorganic solid acid like zeolite is used, the process can be run under a higher temperature and acidity can be adjusted. However, for reactant with large size, holes of a zeolite are too small and mass transfer effect can be formed. Hence, reactions are happened on surface only with a low velocity. If a zeolite having bigger holes is even used, by-effect may be produced owing to the high reaction temperature. Concerning a molecular sieve having middle-size pores, like MCM-41, it is mainly made of silicon dioxide ($SiO_2$) and so has not enough acidity for esterification. If an element like aluminum (Al), zirconium (Zr), titanium (Ti), etc. is introduced to improve acidity, the acidity is still too weak to obtain high esterification activity. If a heteropoly acid (HPA) is loaded on inner surface of a MCM-41, esterification of n-butanol and HOAc can be effectively processed with activity higher than that without-loaded HPA. Yet, water obtained after the reaction will make the HPA be moved and aggregated on the outer surface of MCM-41 to reduce activity of the catalyst. Hence, although solid catalyst is better than liquid catalyst in some way, disadvantages still exist, including acidic points of the catalyst not easily approached by large reactant molecules in the structure and serious declining in activity, and so on. On the contrary, acidic IL has all of the advantages of solid and liquid acids.

For fabricating a Bronsted acid IL, a nitrogen-containing organic compound, like n-butyl imidazole or triphenylphosphine is reacted with 1,4-butane sultone or 1,3-propane sultone to form a white solid zwitterion compound. After purification, the zwitterion compound is reacted with a liquid acid ($H_2SO_4$, $CF_3SO_3H$ or p-$CH_3$—$C_6H_4$—$SO_3H$) to obtain a Bronsted acid IL for esterification of acid and alcohol. For example, synthesis of dioctyl phthalate (DOP) and biodiesel by trans-esterification of cottonseed oil. After the reaction, the product is separated from IL and is taken out by pouring.

The HPA is a kind of super acid, which is a crystal structure composed of heteropoly anions formed by condensation of more than two inorganic oxygen-containing acids and balancing cations. Therein, the heteropoly anion is first grade structure of HPA and Keggin structure is the most stable for wide applications with broad studies. Its structure is a tetrahedron-centered oxide crystal. The heteropoly anion has a general formula as $[XM_{12}O_{40}]^{(x-8)}$, where X is the center atom ($Si^{+4}$, $Ge^{+4}$, $P^{+5}$ or $As^{+5}$); x is its oxidation valence; and M is a metal ion ($Mo^{6+}$, $W^{6+}$ or $V^{6+}$). That is, the center tetrahedron, $XO_4$, is surrounded by 12 octahedron metal oxides. Each octahedron provides 3 oxygen. A common used HPA is 12-HPA, whose formula is $H_3PW_{12}O_{40}$ (Tungstophosphoric Acid, TPA), $H_3PMo_{12}O_{40}$ (Molybdophosphoric Acid, MPA), $H_4SiW_{12}O_{40}$ (Tungstosilicic Acid, TSA) or $H_4SiMo_{12}O_{40}$ (Molybdosilicic acid, MSA). However, HPA is easily dissolved in acid, alcohol and water to form a homogeneous reaction system and cause problems regarding catalyst recycle and facility corrosion. Hence, the prior arts do not fulfill all users' requests on actual use.

SUMMARY OF THE INVENTION

The main purpose of the present invention is to use a Bronsted acid IL as a catalyst to process polyol acetylation for solving problems of product separation, waste acid handling, and corrosion of facilities and improving production through esterification with a green catalysis.

To achieve the above purpose, the present invention is a method of synthesizing polyol acetate by using a catalyst of ionic liquid heteropoly acid, comprising step of: (a) reacting a nitrogen-containing organic compound with an alkyl sultone to obtain a white solid of a zwitterion compound; and then the white solid powder after being purified and dried to be reacted with an HPA in HOAc to obtain a transparent viscous water-tolerable acidic ionic liquid heteropoly acid (IL-HPA); (b) adding a mixture solution of a polyol and HOAc into the IL-HPA and using the polyol and HOAc as feeds and the IL-HPA as a catalyst to process acetylation for obtaining polyol acetate under different reaction conditions; and, (c) recycling HOAc under vacuuming and heating-up; removing water obtained from the reaction; and separating double-phase liquids of an ester product and an IL by staying still, where the ester product is located at upper portion to be taken out; and the IL is located at lower portion to be reused as a catalyst for acetylation. Accordingly, a novel method of synthesizing polyol acetate by using a catalyst of ionic liquid heteropoly acid is obtained.

BRIEF DESCRIPTIONS OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT(S)

The following description of the preferred embodiment is provided to understand the features and the structures of the present invention.

Figure 1:
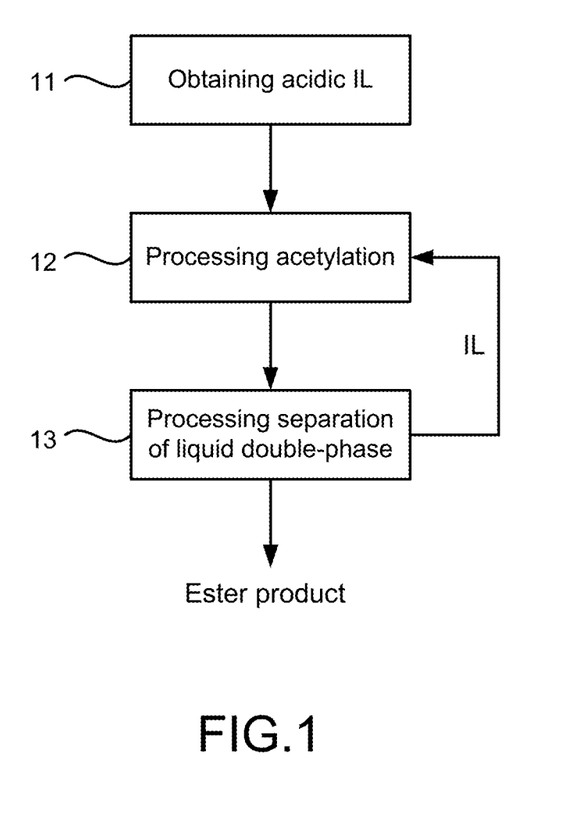
FIG. 1 is the flow view showing the preferred embodiment according to the present invention.

Please refer to FIG. 1, which is a flow view showing a preferred embodiment according to a present invention. As shown in the figure, the present invention is a method of synthesizing polyol acetate by using a catalyst of ionic liquid heteropoly acid (IL-HPA), where Bronsted acidic ionic liquids (IL) are used as a catalyst for acetylations of polyols. The present invention comprises the following steps:

(a) Obtaining acidic IL 11: A nitrogen-containing organic compound, like imidazole, pyridine or alkylamine, is used to be reacted with an alkyl sultone, like 1,3-propane sultone or 1,4-butane sultone, for producing a white solid of a zwitterion compound. Through being purified and dried by ethyl ether, a white solid powder is obtained. Then, a super acid is added to be stirred in acetic acid (HOAc) for 1 hour (hr) at a temperature of 80~105 Celsius degrees (° C.) for obtaining a transparent viscous water-tolerable acidic IL-HPA (also called Bronsted acid IL), where the super acid is a heteropoly acid (HPA), like tungstophosphoric acid (TPA, $H_3PW_{12}O_{40}$), molybdophosphoric acid (MPA, $H_3PMo_{12}O_{40}$), tungstosilicic acid (TSA, $H_4SiW_{12}O_{40}$), or molybdosilicic acid (MSA, $H_4SiMo_{12}O_{40}$); the HPA is processed through a calcination pretreatment at a temperature of 100~450 Celsius degrees (° C.); and a mole ratio of the zwitterion compound to the HPA in the IL-HPA is 1.0~3.0 with a preferred range between 1.5~2.5.

(b) Processing acetylation 12: A mixture solution of a polyol and HOAc is added into the IL-HPA. The polyol and HOAc used as feeds of reactants and the IL-HPA used as a catalyst are obtained for obtaining polyol acetates through acetylation under various reaction conditions. Therein, a mole ratio of the IL-HPA and the polyol is 0.01~0.2; a mole ratio of HOAc to the polyol is 5~40; the reaction conditions include a reaction temperature of 50~200° C. and a reaction time of 0.5~6 hrs; and a reflux of HOAc under a rather high temperature is processed in a closed reaction system.

(c) Processing separation of liquid double-phase 13: After the above reaction, HOAc is recycled through vacuuming and heating-up. Besides, Water obtained from the above reaction is removed. Benzene, toluene or ethyl acetate (EtOAc) can be further added to improve conversion of esterification. By staying still, double-phase liquids of an ester product at upper portion and an IL at lower portion is separated. The ester product can be easily taken out for analysis. The IL can be re-added with a solution of HOAc and a polyol for re-processing the acetylation.

Thus, a novel method of synthesizing polyol acetate by using a catalyst of IL-HPA is obtained.

The polyol is ethylene glycol (EG), propylene glycol (PG), diethylene glycol (DEG) or glycerol (GL). Through the above steps of fabrication, the ester product and the catalyst of the super acid are obtained through separation of liquid double-phase, where the catalyst can be recycled for re-use. Thus, problems of product separation, waste acid handling, and corrosion of facilities can be solved; and, production through esterification can be improved with a green catalysis.

The present invention uses a Bronsted acid IL as a catalyst to effectively process polyol acetylation for producing high boiling-point polar ester solvent like glycerol monoacetate (GMA), glycerol diacetate (GDA), glycerol triacetate (GTA), etc. The present invention uses feeds of a polyol (glycol or glycerol) and HOAc, where HOAc must be overdosed to obtain high conversion. The acetylation has the following reaction formulas:

$$HOCH_2\text{---}CH(OH)\text{---}CH_2OH+ \\ CH_3COOH \rightarrow CH_3COOCH_2\text{---}CH(OR_1)\text{---}CH_2 \\ (OR_2)+H_2O \quad (1)$$

$$HO\text{---}[CH_2CH(R_1)O]_m\text{---}H+ \\ CH_3COOH \rightarrow CH_3COO\text{---}[CH_2CH(R_1)O]_m\text{---} \\ R_2+H_2O \quad (2)$$

Therein, in the reaction formula (1), $R_1$ and $R_2$ are hydrogen group (—H) or acyl group (—$OCCH_3$); in the reaction formula (2), $R_1$ is hydrogen group (—H) or methyl group (—$CH_3$) and $R_2$ is hydrogen group (—H) or acyl group (—$OCCH_3$); and, m is 1~3.

The present invention uses a Bronsted acid IL to process acetylation under different reaction conditions. After acetylation, separation of liquid double-phase is processed to obtain ether compounds, where the IL is recycled after removing HOAc and water to be reused in acetylation.

The acidic IL is obtained from a reaction of a sulfonic zwitterion compound and an HPA. The zwitterion compound obtained from a reaction of an imidazole-type, a pyridine-type or an alkylamine-type nitrogen-containing compound and an alkyl sultone, having a structure of Therein, the nitrogen-containing compounds of alkylimidazole, alkylpyridine and alkylamine have alkyl groups of $R_1$, $R_2$ and $R_3$ all having a formula of $C_mH_{2m+1}$, $_{m=1~18}$; and n is 3~6.

Figure 2:
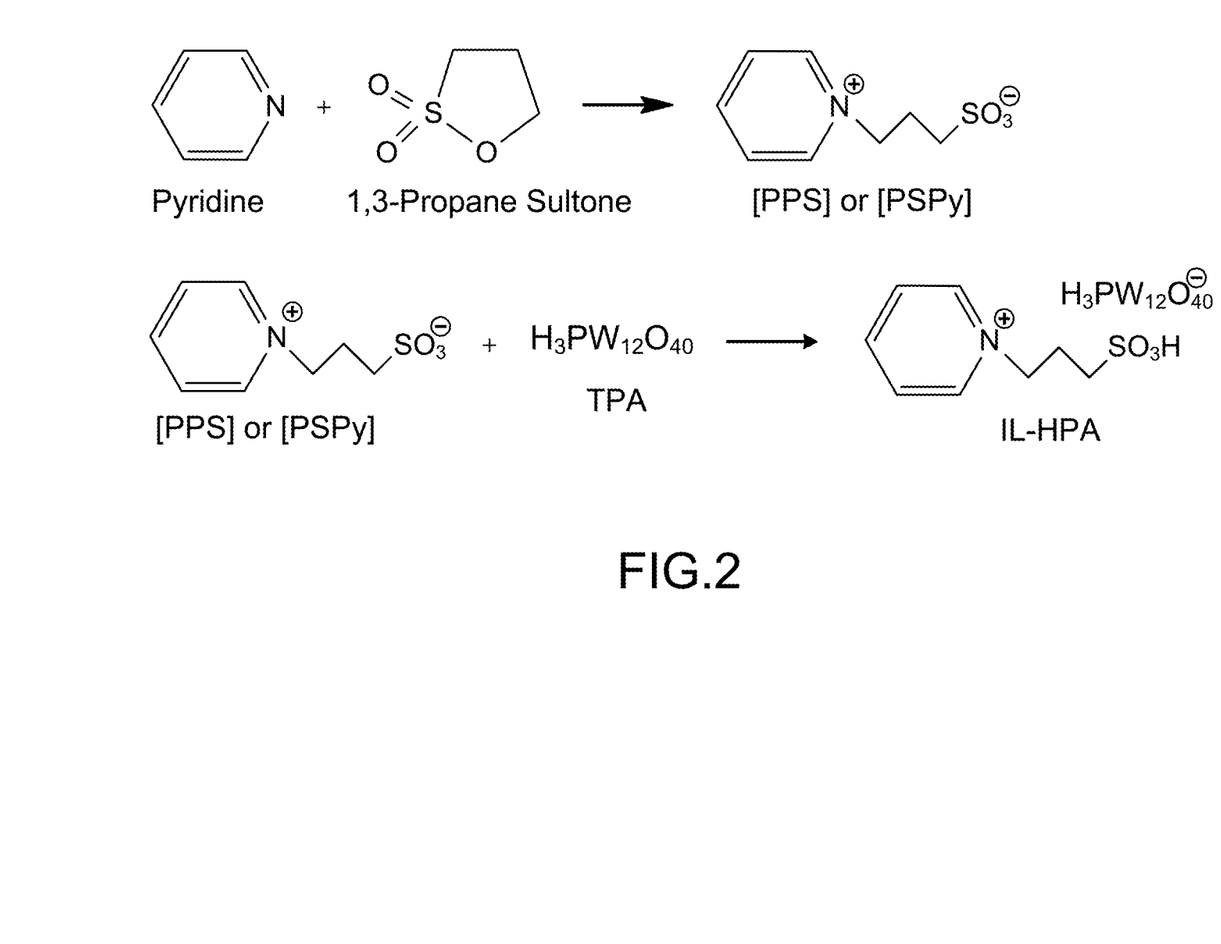
FIG. 2 is the view showing the reaction for fabricating the acidic IL.

Please refer to FIG. 2 to FIG. 10, which are a view showing a reaction for fabricating the acidic IL; a view showing batch reactions; views showing effects of PPS/TPA ratio, TPA sintering temperature, HOAc/GL ratio, IL amount, and reaction temperature and reaction time on esterification activity; a view showing reusability of catalyst; and a view showing esterification activities of different polyols. As shown in the figures, on using the present invention, for fabricating an acidic IL, pyridine or n-butyl imidazole is reacted with 1,3-propane sultone at 40° C. for 24 hrs to obtain a white solid of a zwitterion compound. After being purified with ethyl ether and dried through vacuuming, $R^+$—$(CH_2)_3$—$SO_3^-$ (n-propane sulfonic acid pyridinium (PSPy) or pyridinium propyl sulfobetaine, (PPS)) is obtained, where R is pyridine or n-butyl imidazole. An amount of the white solid is put into a round bottomed flask to be added with 1~3 times amount of tungstophosphoric acid (TPA, $H_3PW_{12}O_{40}$-$nH_2O$). After being stirred at 100° C. for 0.5 hrs, a transparent viscous IL is eventually formed. Then, toluene and ethyl ether are used to wash out impurities except the IL. After being dried through vacuuming, an acidic IL-HPA of $[R^+$—$(CH_2)_3$—$SO_3H]$ $[H_2PW_{12}O_{40}$-$nH_2O]^-$ is obtained, as shown in FIG. 2.

Figure 3:
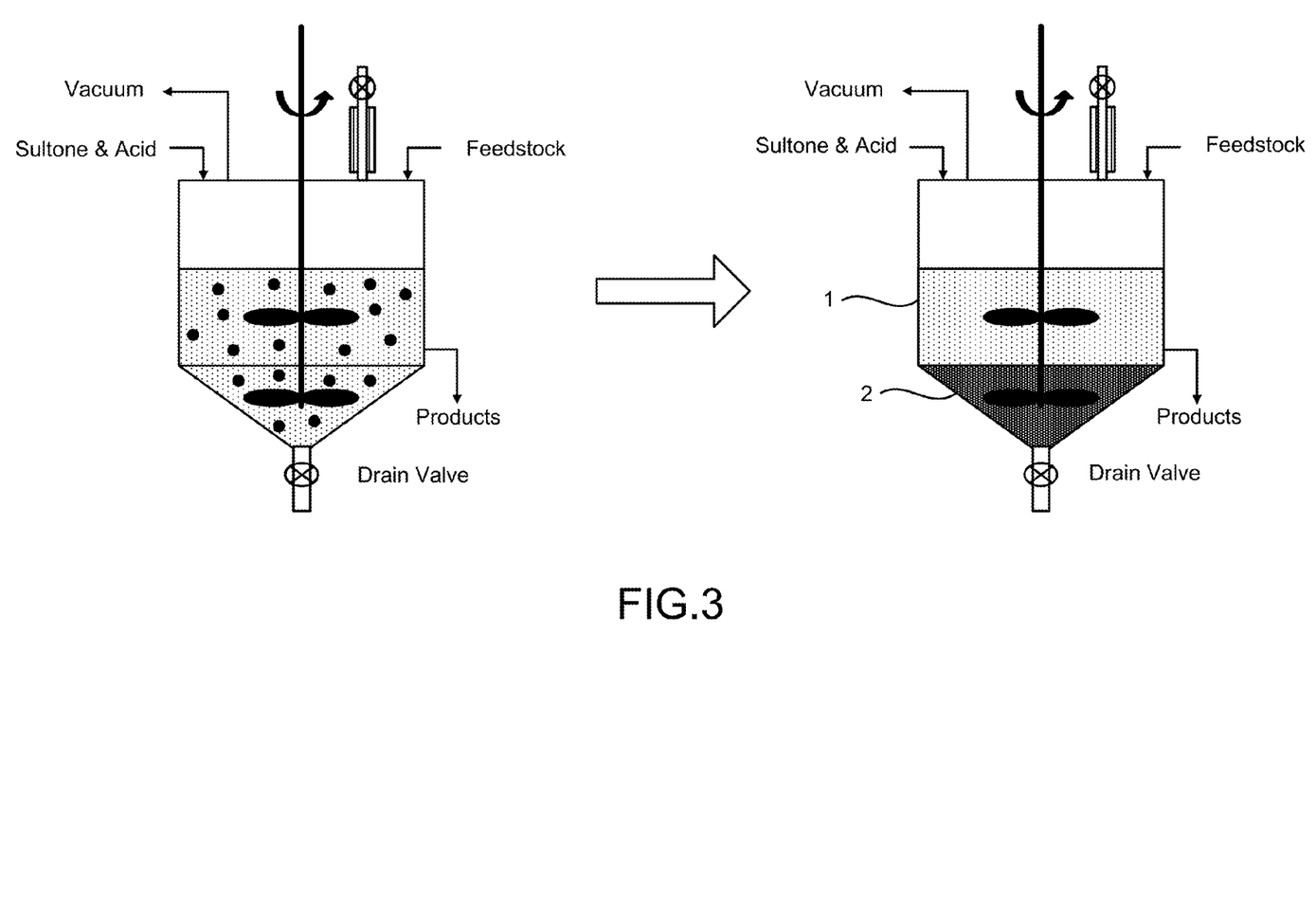
FIG. 3 is the view showing the batch reactions.

On processing acetylation, a mixture solution of a polyol and HOAc is poured into the viscous IL-HPA to be reacted in a water bath under a stirring velocity of 400 rounds per minute (rpm) for a fast reaction. After the reaction, the total solution is stayed still for separation of liquid double-phase. A product 1 at upper portion is taken out for analysis. A gas chromatographer (GC) is used to acquire characteristics of components of the product, i.e. conversion rate of polyol and selectivity of ester product. The reaction conditions include a temperature of 50~200° C., a HOAc/polyol ratio of 5~40, an IL-HPA/polyol mole ratio of 0.01~0.2 and a reaction time of 0.5~6 hrs. For acquiring reusability of the IL, after the reaction and the separation of liquid double-phase, the IL 2 at lower portion is vacuumed at 85° C. and extra HOAc and water formed during the reaction are removed. Then, new feeds are added for next reaction. Or, after the reaction, HOAc is recycled through vacuuming under heating-up; water obtained is removed; after staying still, separation of liquid double-phase is processed; and the IL is reused as a catalyst for next reaction. As shown in FIG. 3, the left part shows esterification of the IL and the right part shows the separation of liquid double-phase after removing HOAc and water.

[State-of-Use 1] Testing Activity of Esterification

Solid powders of 706 g (0.0035 mole) of PPS and 5.75 g (0.00175 mole) of un-dried TPA are mixed to be added with 11 g (0.175 mole) of HOAc to be stirred in an oil bath at 105° C. for 10 minutes (min) for forming two layers of immiscible transparent liquids, where the lower layer is a flowing IL. Then, a mixture solution of 11 g (0.175 mole) of HOAc and 3.22 g (0.035 mole) of GL is added to be further stirred at 105° C. for 2 hrs. After reaction, the flask is put on a rotavapor to remove out HOAc and water. Then, two layers of liquids are separated through staying still. The upper layer is a clear ester product; and, the lower layer is a flowing IL. The liquid at the upper layer is taken out to be analyzed with GC for ester products (GMA, GDA and GTA) with mole ratios figured out. When mole ratio (mole %) of GTA is higher and mole % of GMA is lower, it means that the catalysis system has a higher esterification activity. The present invention has a GL conversion almost close to 100% with mole % of GMA, GDA and GTA as 3.7%, 46.3% and 50.0%, respectively.

[State-of-Use 2] Effect of PPS/TPA Ratio on Esterification Activity

Figure 4:
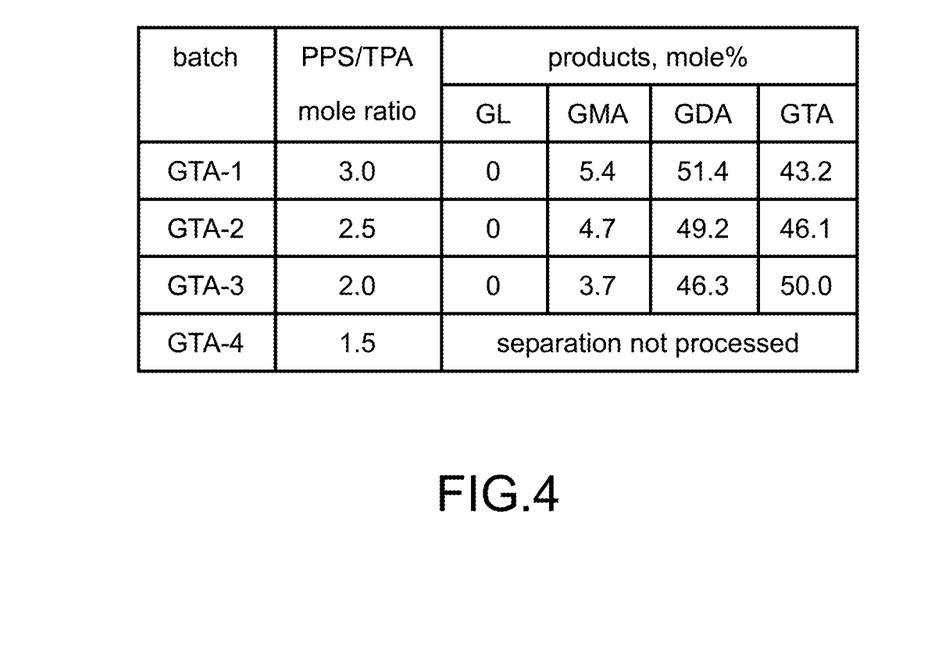
FIG. 4 is the view showing the effect of the PPS/TPA ratio on esterification activity.

By using the method as described in the state-of-use 1, mole % of PPS/TPA is changed into 3.0, 2.5, 2.0, 1.5 and 1.0 for testing activity of esterification. Therein, mole % of HOAc/GL is 10; mole % of TPA/GL is 0.05; reaction temperature is 105° C.; and, reaction time is 2 hrs. As shown in FIG. 4, for TPA without remove absorbed water, only an IL having a PPS/TPA mole % higher than 2.0 is able to form liquid double-phase after removing HOAc and water. The lower layer of the liquid double-phase is a colorless transparent IL with a viscosity increased following increase of the PPS/TPA mole %. Yet, if the IL has a PPS/TPA mole % lower than 2.0, the IL and the final product will not be formed into liquid double-phase after removing HOAc. Besides, as the PPS/TPA mole % is increased, esterification activity of the IL is decreased for obtaining better separation of liquid double-phase. Hence, an IL having a PPS/TPA mole % of 2.0 is the best choice.

[State-of-Use 3] Effect of TPA Sintering Temperature on Esterification Activity

Figure 5:
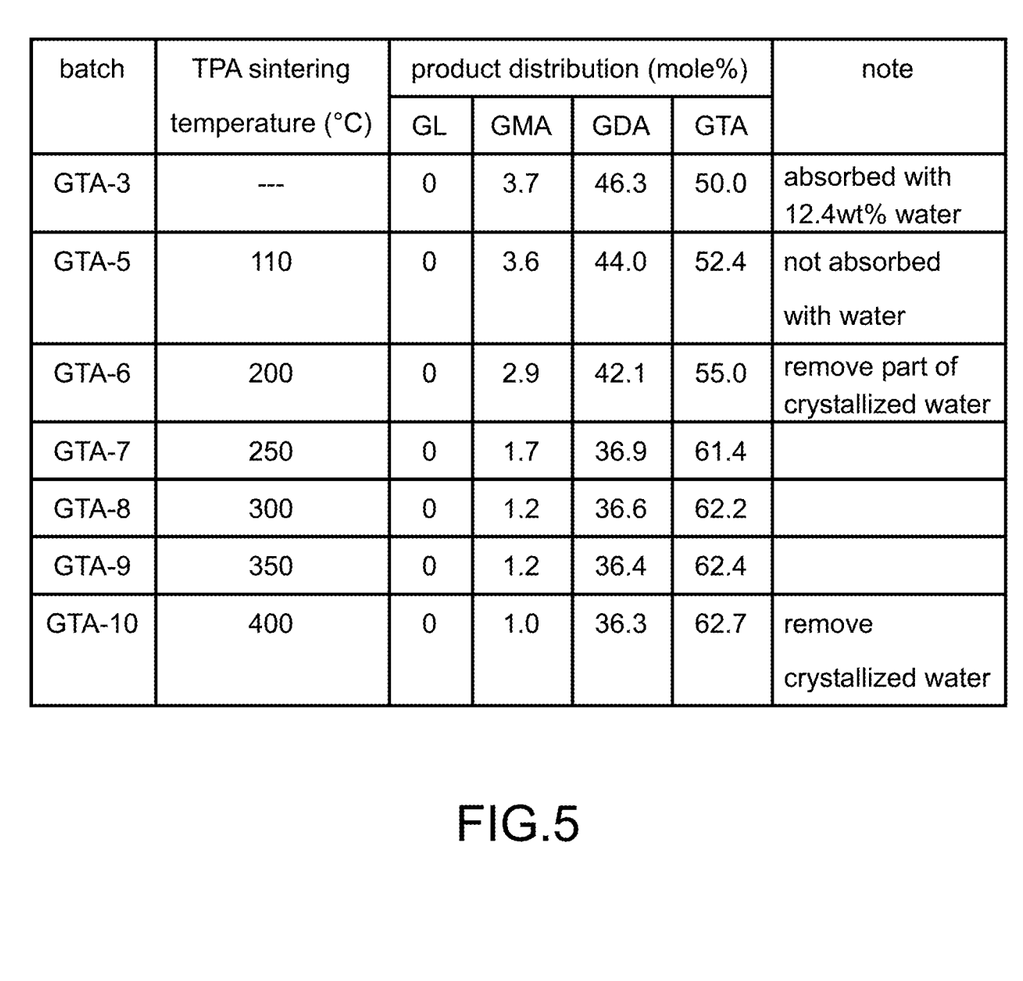
FIG. 5 is the view showing the effect of the TPA sintering temperature on esterification activity.

By using the method as described in the state-of-use 1, a TPA sintering temperature is changed into 110° C., 200° C., 250° C., 300° C., 350° C. and 400° C. for testing activity of esterification. Therein, mole % of PPS/TPA is 2.0; mole % of HOAc/GL is 10; mole % of TPA/GL is 0.05; reaction temperature is 105° C.; and, reaction time is 2 hrs. As shown in FIG. 5, following increase of the TPA sintering temperature, esterification activity increases. When the temperature is higher than 250° C., a stable and high activity is achieved; yet, the IL at the lower layer is changed into a flowing, uniform and light-yellow turbid liquid. Hence, a preferred sintering temperature is 200~350° C.

[State-of-Use 4] Effect of HOAc/GL Ratio on Esterification Activity

Figure 6:
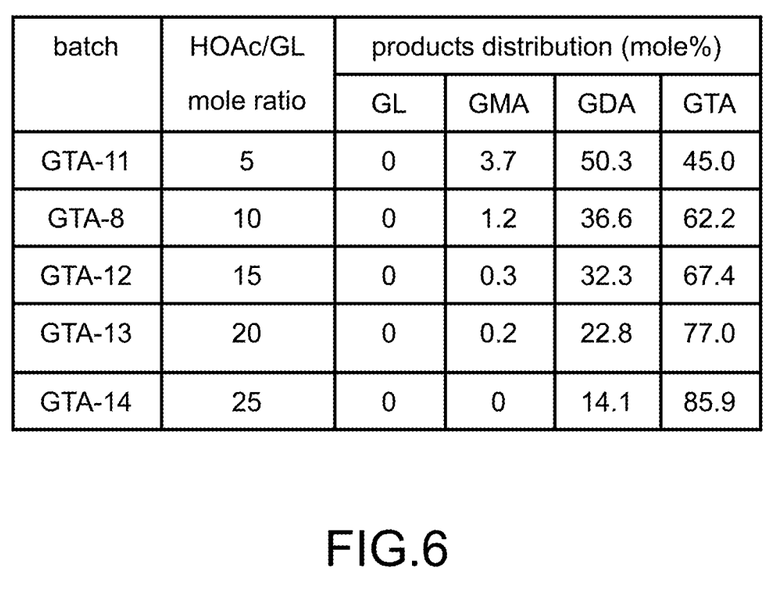
FIG. 6 is the view showing the effect of the HOAc/GL ratio on esterification activity.

By using the method as described in the state-of-use 1, mole % of HOAc/GL is changed into 5, 10, 15 and 20 for testing activity of esterification. Therein, mole % of PPS/TPA-300H is 2.0; TPA-300H is the TPA sintered at 300° C.; catalyst amount is 5 mole % to GL; reaction temperature is 105° C.; and, reaction time is 2 hrs. As shown in FIG. 6, the conversion of esterification of the IL is increased following increase of the HOAc/GL mole %; but, a too high HOAc/GL mole % would recycle a great amount of HOAc. Hence, a preferred HOAc/GL mole % is 15~20.

[State-of-Use 5] Effect of IL Amount on Esterification Activity

Figure 7:
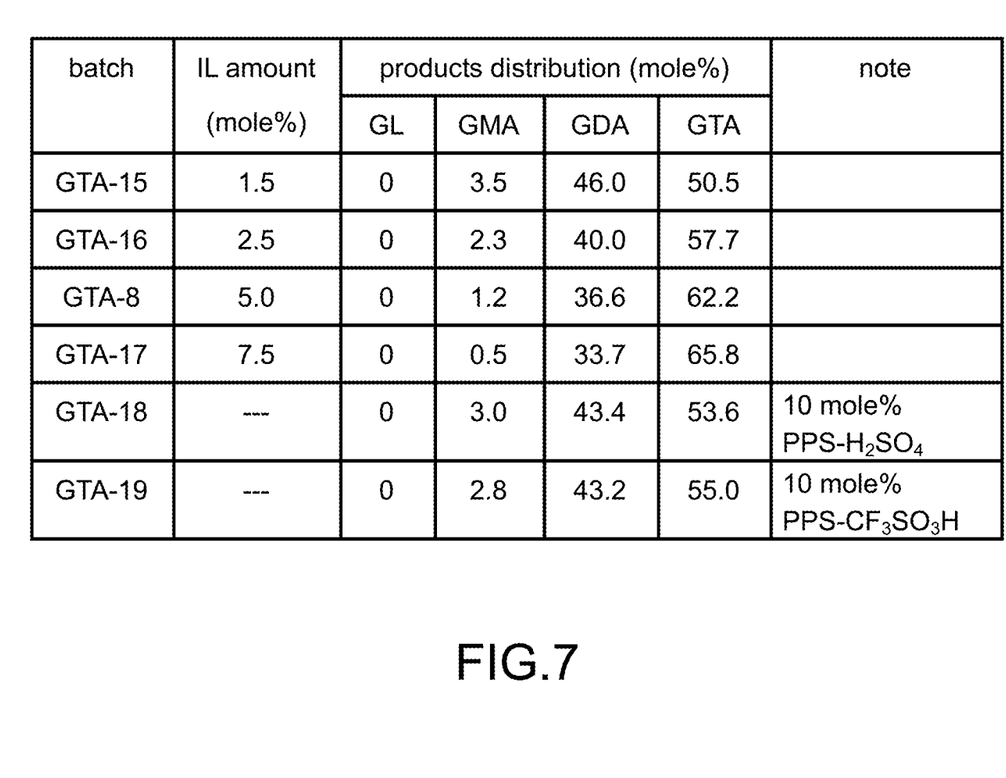
FIG. 7 is the view showing the effect of the IL amount on esterification activity.

By using the method as described in the state-of-use 1, mole % of PPS/TPA-300H is 2.0 and the catalyst amount is changed into 2.5 mole %, 5.0 mole % and 7.5 mole % to GL for testing activity of esterification. Therein, mole % of HOAc/GL is 10; reaction temperature is 105° C.; and, reaction time is 2 hrs. As shown in FIG. 7, conversion of esterification is increased following increase of the TPA amount; but, a too high TPA amount would hinder separation of liquid double-phase of the IL and the product. Besides, on comparing two acids (sulfuric acid ($H_2SO_4$) and trifluorosulfonic acid ($CF_3SO_3H$)) concerning esterification activity and selectivity, activity of 2.5 wt % PPS-TPA is better than that of 10 mole % PPS—$H_2SO_4$ in an IL catalyst system. Hence, a preferred amount of catalyst is 2.5~7.5 mole % to GL.

Figure 8:
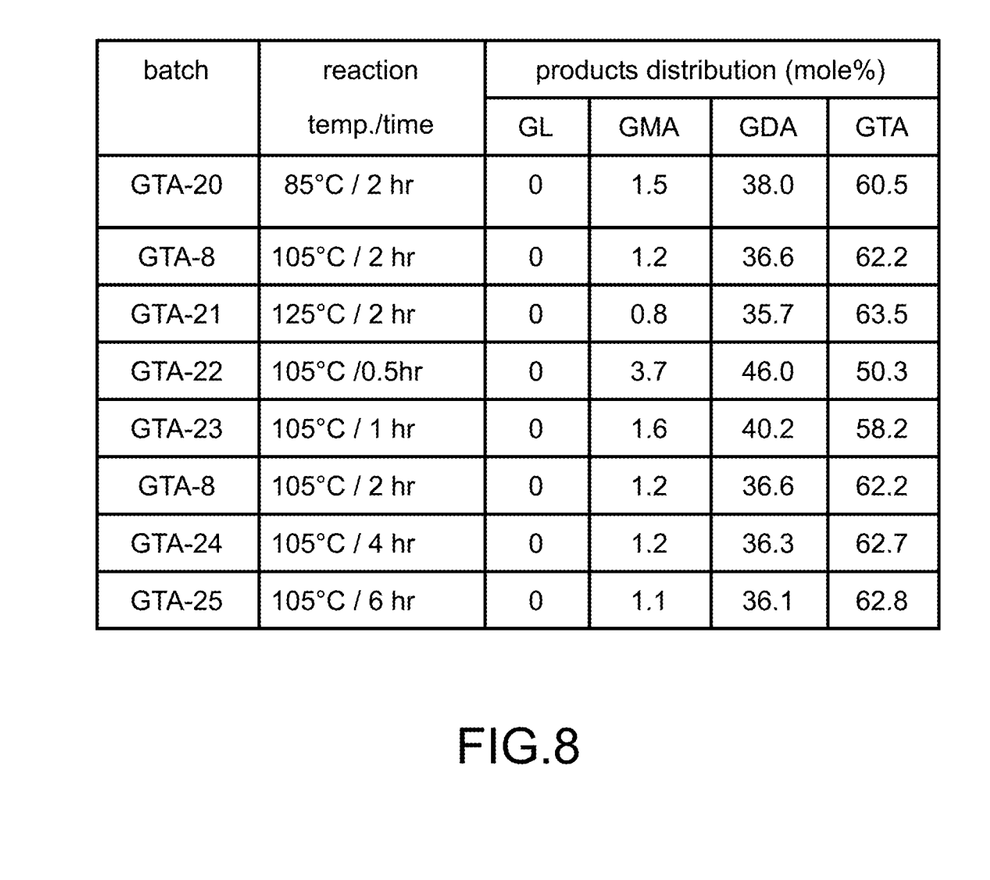
FIG. 8 is the view showing the effect of the reaction temperature and the reaction time on esterification activity.

[State-of-Use 6] Effect of Reaction Temperature and Reaction Time on Esterification Activity By using the method as described in the state-of-use 1, ratio of PPS/TPA-300H in the catalyst system is 2; catalyst amount is 5 mole %; and, ratio of HOAc/GL is 10. Under different reaction temperatures and reaction times, esterifications are processed. As shown in FIG. 8, esterification activity is increased following increase of the reaction temperature; but, a too high reaction temperature makes the IL become a light-blue flowing turbid liquid. Besides, if the reaction time is more than 4 hrs, conversion of esterification stops increasing. Hence, a preferred reaction temperature is 80120° C. and a preferred reaction time is 1~2 hrs.

[State-of-Use 7] Test on Reusability of Catalyst

Figure 9:
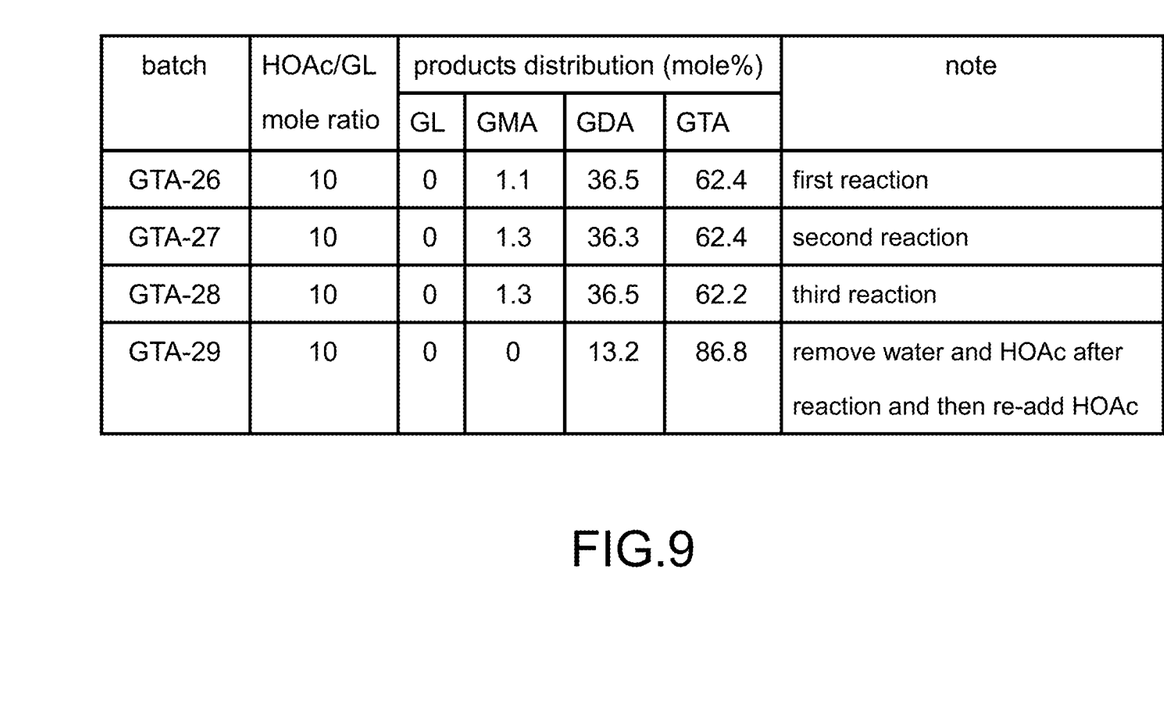
FIG. 9 is the view showing the reusability of the catalyst.

By using the method as described in the state-of-use 1, ratio of PPS/TPA-300H in the catalyst system is 2; catalyst amount is 5 mole %; ratio of HOAc/GL is 10; reaction temperature is 105° C.; and, reaction time is 2 hrs. After reaction, a rotavapor is used to remove HOAc and water under vacuuming and heating-up. By staying still, separation of liquid double-phase is processed. The product at upper layer is taken out and the IL is kept in the flask to be added with a new batch of reactant solutions for repeated reactions under the same reaction conditions. As shown in FIG. 9, the IL-HPA (PPS-TPA) is reused without obvious declination on activity. Besides, after removing HOAc and water after the reaction, new HOAc is added for reaction again with an improvement on GTA amount to 86.8%.

[State-of-Use 8] Comparison on Esterification Activities of Different Polyols

Figure 10:
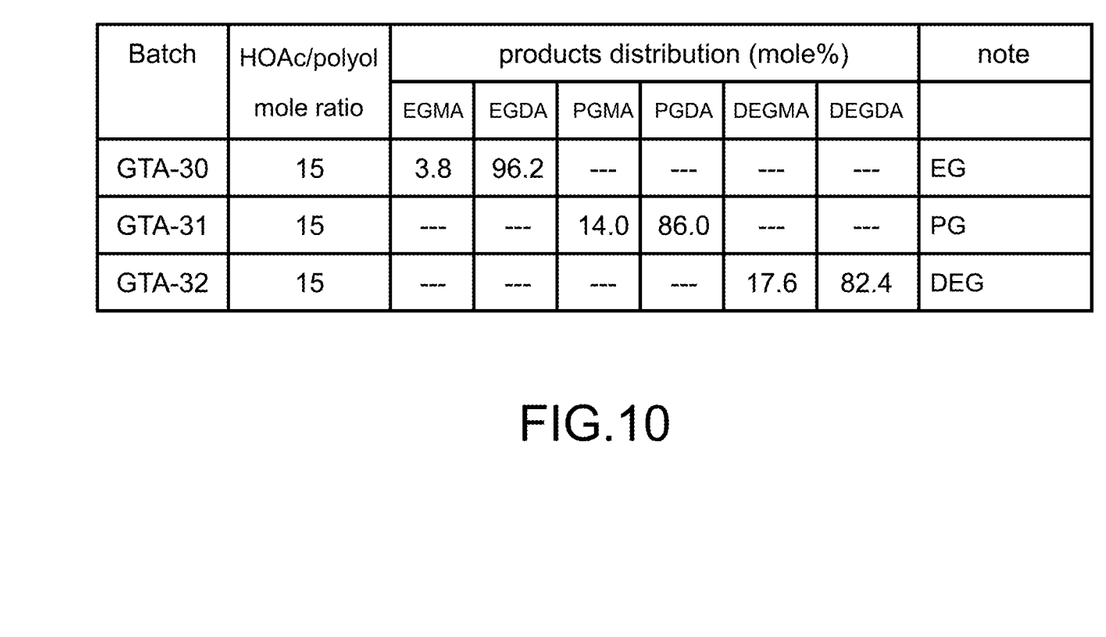
FIG. 10 is the view showing the esterification activities of different polyols.

By using the method as described in the state-of-use 1, ratio of PPS/TPA-300H in the catalyst system is 2; catalyst amount is 5 mole %; and, ratio of HOAc/polyol is 50. Therein, the polyol is ethylene glycol (EG), propylene glycol (PG) or diethylene glycol (DEG); reaction temperature is 105° C.; and, reaction time is 2 hrs. On using EG as a feed, the product is ethylene glycol monoacetate (EGMA) and ethylene glycol diacetate (EGDA); on using PG, propylene glycol monoacetate (PGMA) and propylene glycol diacetate (PGDA); and, on using DEG, diethylene glycol monoacetate (DEGMA) and diethylene glycol diacetate (DEGDA). As shown in FIG. 10, EG, PG and DEG use the IL-HPA catalyst system for effective esterification of HOAc, where their esterification activities are EG>PG>DEG and are all higher than the esterification activity of GL.

To sum up, the present invention is a method of synthesizing polyol acetate by using a catalyst of ionic liquid heteropoly acid, where a Bronsted acid IL is used as a catalyst for acetylation of polyol; products and the catalyst of super acid is processed through separation of liquid double-phase; the catalyst can be recycled for solving problems of product separation, waste acid handling, and corrosion of facilities; and, thus, production through esterification can be improved with a green catalysis.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of synthesizing polyol acetate by using a catalyst of ionic liquid heteropoly acid, comprising steps of:
   (a) reacting a nitrogen-containing organic compound with an alkyl sultone to obtain a white solid of a zwitterion compound; and said white solid powder after being purified and dried to be reacted with a heteropoly acid (HPA) in acetic acid (HOAc) to obtain a transparent viscous water-tolerable acidic ionic liquid heteropoly acid (IL-HPA),
      wherein said HPA is processed through calcination pre-treatment at a temperature of 100~450 Celsius degrees (° C.); and a mole ratio of said zwitterion compound to said HPA in said IL-HPA is 1.0~3.0;
   (b) adding a mixture solution of a polyol and HOAc into said IL-HPA and using said polyol and HOAc as feeds and said IL-HPA as a catalyst to process acetylation to obtain polyol acetate under different reaction conditions,
      wherein a mole ratio of said IL-HPA to said polyol is 0.01~0.2; a mole ratio of HOAc to said polyol is 5~40; and said reaction conditions include a reaction temperature of 50~200° C. and a reaction time of 0.5~6 hours (hrs); and
   (c) recycling HOAc under vacuuming and heating-up; removing water obtained from the above reaction; and separating double-phase liquids of an ester product and an ionic liquid (IL) by staying still,
      wherein said ester product is located at upper portion to be taken out; and said IL is located at lower portion to be reused as a catalyst for acetylation.

2. The method according to claim 1, wherein said HPA is a catalyst and is selected from a group consisting of tungstophosphoric acid (TPA, $H_3PW_{12}O_{40}$), molybdophosphoric acid (MPA, $H_3PMo_{12}O_{40}$), tungstosilicic acid (TSA, $H_4SiW_{12}O_{40}$) and molybdosilicic acid (MSA, $H_4SiMo_{12}O_{40}$).

3. The method according to claim 1, wherein, in step (a), said nitrogen-containing organic compound is a nitrogen-containing compound of a type selected from a group consisting of an imidazole type, a pyridine type and a trialkylamine type; and said alkyl sultone is selected from a group consisting of 1,3-propane sultone or 1,4-butane sultone.

4. The method according to claim 3, wherein said nitrogen-containing compound is selected from a group consisting of alkylimidazole, alkylpyridine and alkylamine; and said alkyl group in nitrogen-containing compound contains $C_mH_{2m+1}, m=1~18$.

5. The method according to claim 3, wherein said alkyl group in alkyl sultone contains $C_nH_{2n}, n=3~6$.

6. The method according to claim 1, wherein said polyol is selected from a group consisting of ethylene glycol (EG), diethylene glycol (DEG), propylene glycol (PG) and glycerol (GL).

7. The method according to claim 1, wherein said HPA is sintered at a preferred temperature of 200~350° C.

8. The method according to claim 1, wherein a preferred mole ratio of said zwitterion compound to said HPA in said catalyst of IL-HPA is 1.5~2.5.

9. The method according to claim 1, wherein a preferred mole ratio of HOAc to said polyol is 15~20.

10. The method according to claim 1, wherein a preferred mole ratio of said catalyst of IL-HPA to said polyol is 025~0.075.

11. The method according to claim 1, wherein a preferred temperature for said reaction of acetylation is 80~120° C.

12. The method according to claim 1, wherein a preferred time period for said reaction of acetylation is 1~2 hrs.

13. The method according to claim 1, wherein a water-removing agent is further added to improve conversion of esterification and said a water-removing agent is selected from a group consisting of benzene, toluene and ethyl acetate (EtOAc).

* * * * *